(12) United States Patent
Verbruggen et al.

(10) Patent No.: US 7,988,962 B2
(45) Date of Patent: Aug. 2, 2011

(54) USE OF POLYSULPHATED ALGINATE IN CELLULAR MATRICES

(75) Inventors: August Verbruggen, Eke-Nazareth (BE); Eric Veys, Zwijnaarde (BE)

(73) Assignee: Universiteit Gent (BE)

( * ) Notice: Subject to any disclaimer, the term of this patent is extended or adjusted under 35 U.S.C. 154(b) by 719 days.

(21) Appl. No.: 10/595,821

(22) PCT Filed: Dec. 2, 2004

(86) PCT No.: PCT/BE2004/000171
§ 371 (c)(1),
(2), (4) Date: Jan. 16, 2007

(87) PCT Pub. No.: WO2005/054446
PCT Pub. Date: Jun. 16, 2005

(65) Prior Publication Data
US 2007/0128173 A1    Jun. 7, 2007

Related U.S. Application Data

(60) Provisional application No. 60/526,492, filed on Dec. 2, 2003.

(51) Int. Cl.
*A01N 63/00* (2006.01)
(52) U.S. Cl. .................................... 424/93.7
(58) Field of Classification Search .................. None
See application file for complete search history.

(56) References Cited

U.S. PATENT DOCUMENTS

| 5,705,177 | A | 1/1998 | Roufa et al. |
| 5,705,178 | A | 1/1998 | Roufa et al. |
| 5,994,325 | A | 11/1999 | Roufa et al. |
| 6,020,326 | A | 2/2000 | Roufa et al. |
| 6,083,930 | A | 7/2000 | Roufa et al. |
| 6,127,348 | A | 10/2000 | Roufa et al. |
| 6,417,173 | B1 | 7/2002 | Roufa et al. |
| 6,756,362 | B2 | 6/2004 | Roufa et al. |
| 2003/0109493 | A1 | 6/2003 | Maximillen et al. |
| 2003/0161884 | A1* | 8/2003 | Rosenberg et al. ............ 424/486 |

FOREIGN PATENT DOCUMENTS

| EP | 1 027 893 A | 8/2000 |
| WO | WO 98/11141 A | 3/1998 |

OTHER PUBLICATIONS

Kavalkovich et al., In vitro Cell. Dev. Biol.—Animal, 2002, vol. 38, p. 457-466.*
Ronghua et al., Carbohydrate Polymers, Apr. 2003, vol. 52, p. 19-24.*
Kawada et al., Arch Dermatol Res, 1999, vol. 291, p. 542-547.*
Rihova B., Advanced Drug Delivery Reviews, 1996, vol. 21, p. 157-176.*
Verbruggen et al., J Rheumatol., 1999, vol. 26, p. 1663-1671.*
Hauselmann et al., American Journal of physiology, 1996, vol. 271, p. C742-C752.*
Almqvist et al., "Culture of Chondrocytes in Alginate Surrounded by Fibrin Gel: Characteristics of the Cells Over a Period of Eight Weeks," Annals, of Rheumatic Diseases 60: 781-790 (2001).
Schwelger et al., Polysaccharide Sulfates II Sulfuric Acid Esters of Glycuronans Having Various Degrees of Substitution 21:275-281 (1972).
Verbruggen et al., "Influence of Polysulfated Polysaccharides on Aggrecans Synthesized by Differentiated Human Articular Chondrocytes," The Journal of Rheumatology 26:1663-1671 (1999).
International Search Report (PCT/BE2004/000171) (mailed Jun. 27, 2005).
Written Opinion of the International Searching Authority (PCT/BE2004/000171) (mailed Jun. 27, 2005).
Astrup, T. et al., "Polysaccharide Sulfuric Acids as Anticoagulants," *Acta Phys. Scand.* 8: 215-226, 1944.
McPherson et al., "Articular Cartilage Injury," Langer, R., Lanza, RP., & Vacanti, J. (Eds.) Principles of Tissue Engineering, Second Edition. *Acad. Press* 697-709, 2000.
Sledge, "Microfracture Techniques in the Treatment of Osteochondral Injuries," *Clin. Sports Med.* 20: 1-15, 2001.
Steadman et al., "Microfracture: Surgical Technique and Rehabilitation to Treat Chondral Defects," *Clin Ortho. and Related Research* 391S: S362-S369, 2001.
*The Merck Index: An Encyclopedia of Chemicals, Drugs, and Biologicals*, 12th ed. Budavari, S.; O'Neal, M.J.; Smith, A.; Heckelman, P.E.; Kinneary, J.F., Eds.; Merck & Co.: Whitehouse Station, NJ, p. 45, 1996.

* cited by examiner

*Primary Examiner* — Kade Ariani
(74) *Attorney, Agent, or Firm* — Clark & Elbing LLP

(57) ABSTRACT

The present invention describes an in vitro/ex vivo method for the cultivation of connective tissue cells or progenitor cells (e.g. chondrogenic cells) in matrix comprising polysulphated alginate. These cultivated cells can be used in the preparation of a medicament for the treatment or prevention of osteochondral defects. The invention also describes a matrix comprising polysulphated alginate and mammalian connective tissue cells or progenitor cells thereof.

17 Claims, 1 Drawing Sheet

USE OF POLYSULPHATED ALGINATE IN CELLULAR MATRICES

CROSS-REFERENCE TO RELATED APPLICATIONS

This application is the U.S. National Stage of International Application No. PCT/BE2004/000171, filed Dec. 2, 2004, which, in turn, claims the benefit of U.S. Provisional Patent Application Ser. No. 60/526,492 filed on Dec. 2, 2003.

FIELD OF THE INVENTION

The present invention relates to matrices, more particularly matrices for use in the repair of osteochondral defects, as well as pharmaceutical products comprising these matrices.

BACKGROUND

The therapeutical use of polysulphated polysaccharides has been extensively studied over the past fifteen years. Upon sulphation of their hydroxyl groups, polysaccharides acquire particularly interesting biological activities.

Polysulphated cyclodextrins have been shown to reduce or to block the effects of teratogenic substances on foetal development (WO 91/16905), to improve tissue scar formation (WO 93/09790), to impair retroviral (HIV) replication (EP 447171) and to inhibit angiogenesis (WO 89/06536).

Polysulphated inulin has been shown to be an efficient inhibitor of the Complement system (U.S. Pat. No. 4,021, 545; Immunol. 1965, 8:29; Pharmacology 1973, 9:74) and possesses anti-lipaemic properties (Arch. Int. Pharmacodyn. 1954, XCIX: 334.

Alginic acid sulphate has been shown to possess anticoagulant properties (U.S. Pat. Nos. 3,766,167 and 4,331,697) and has been proposed as an antithrombic resin composition in combination with synthetic resins (U.S. Pat. No. 4,822, 615). Alginic acid sulphate was shown to inhibit retroviruses and was proposed as a substance to topically cleanse the human body (U.S. Pat. No. 5,100,879) and as a method of treatment of diseases (T-cell infections) caused by retroviruses (U.S. Pat. No. 4,840,941).

Sulphated pectinic acid has been used as non-absorbable synthetic sulphated polysaccharide to decrease cholesterol and fatty acid absorption (U.S. Pat. Nos. 5,616,570 and 5,063, 210) and was found to inhibit pancreatic cholesterol esterase (U.S. Pat. No. 5,484,777).

Polysulphated glycosaminoglycans such as chondroitin polysulphate have been found to stimulate the production of extracellular matrix macromolecules (hyaluronan, chondroitin sulphate proteoglycan) by connective tissue cells (synovial cells, fibroblasts, articular cartilage cells) (Acta Rheumatol. 1977, 1:75; J. Rheumatol. 1979, 6:554; J. Rheumatol. 1999, 26:1663).

Chondrocytes are incapable of repairing endochondral lesions of articular cartilage and these lesions inevitably lead to the development of osteoarthritis. Attempts at repairing enchondral lesions of articular cartilage by implantation of human autologous chondrocytes have been proposed with limited success (N. Engl. J. Med. 1994, 331:889). It has been demonstrated that implantation of human chondrocytes in biocompatible and biodegradable hydrogel grafts improves the possibilities to restore these articular cartilage lesions (PNAS 2002, 99:9996-10001;. Ann NY Acad Sci, 2002, 961: 118-122).

The technique of chondrocyte culture in alginate beads glued together with fibrin gel has been described recently (Ann. Rheum. Dis. 2001, 60 781-790). In this culture condition, chondrocytes colonize the whole alginate/fibrin hydrogel and form a hyaline-like cartilagineous tissue.

SUMMARY OF THE INVENTION

The invention is based on the observation that polysulphated alginate, when present in a matrix, has a beneficial effect on the proliferation and production of extracellular matrix components by connective tissue cells. Thus, the present invention relates to the use of polysulphated alginate as a matrix-component in the treatment or prevention of osteochondral defects.

A first aspect of the invention relates to a matrix comprising polysulphated alginates for use in the repair of osteochondral defects. The matrix can further comprise one or more other components such as, but not limited to, gelling agents, nutrients and antibiotics. More particularly, the matrix can further comprise a chemotactic agent which attracts connective tissue cells to the matrix.

A particular embodiment of the invention relates to a matrix comprising polysulphated alginates and further comprising an unsulphated polysaccharide gel. In a more particular embodiment the unsulphated polysaccharide is alginate. Specific embodiments of the invention relate to a matrix comprising an alginate gel and further comprising between about 0.5 mg and 100 mg polysulphated alginate/gram unsulphated alginate.

It was further observed that artificial matrices comprising polysulphated alginate are suitable for the culture of cells, more particularly human articular cartilage cells. Moreover, the presence of polysulphated alginate in the artificial matrix greatly induces the production of ECM components by chondrocytes.

Thus, a second aspect of the present invention relates to the use of polysulphated alginate as a matrix component for the cultivation or as a carrier for human or animal cells, more particularly connective tissue cells or precursors thereof, particularly osteochondral cells. Polysulphated alginate is of particular use as a matrix component for chondrogenic cells, particularly articular cartilage cells (chondrocytes).

A particular embodiment of the invention relates to the use of polysulphated alginate as a matrix-component for human or animal cells to be implanted into the human or animal body. More particularly, polysulphated alginate is of use in matrices for cells to be implanted in the context of repair or remodeling of the animal or human body.

A particular aspect of the invention relates to the use of polysulphated alginate as a matrix-component and/or carrier for human or animal cells to be implanted into the human or animal body in the context of the repair of an osteochondral defect. Osteochondral cells embedded in these artificial matrices comprising polysulphated alginates are of use in the repair superficial lesions of osteo-arthritic cartilage.

Another aspect of the present invention relates to an in vitro method for the cultivation of connective tissue cells or precursors thereof (mesenchymal stem cells) comprising the step of contacting said cells with a matrix comprising polysulphated alginate.

Moreover, the present invention relates to an in vitro method for stimulating aggrecan synthesis by osteochondral cells or progenitors, said method comprising contacting said cells with polysulphated alginate.

Thus, the present invention relates to a pharmaceutical composition containing a matrix comprising polysulphated alginate for use in the repair of osteochondral defects. The pharmaceutical composition can further comprise other components such as connective tissue cells or precursors thereof, such as mesenchymal stem cells, but more particularly osteochondral cells, most particularly chondrogenic cells.

Polysulphated alginate can be delivered as a sterile and endotoxin-free, ready-to-use injectable gel for the transplantation of animal or human articular chondrocytes or other animal or human connective tissue cells.

According to a particular embodiment the pharmaceutical composition comprises a matrix, which comprises a concentration of polysulphated alginate in the range of between about 100 ng/ml and about 500 µg/ml.

The present invention further relates to the use of polysulphated alginate in the production of a medicament for the treatment or prevention of osteochondral defects. More particularly, the medicament is in the form of a matrix which can comprise other components such as connective tissue cells or precursors thereof.

DETAILED DESCRIPTION

Alginic acid is a linear heteropolysaccharide occurring naturally in seaweeds and some bacteria. It is a block copolymer of repeating units of β(1-4)D-mannuronic acid (M) and α(1-4)L-guluronic acid (G). 'Alginate(s)' as used herein refers to one or more salts (and/or esters) of this polysaccharide. The proportion as well as the distribution of the two monomers determines to a large extent the physiochemical properties of alginate. The M- and G-residues are joined together in a blockwise fashion. This implies that three types of blocks may be found, homopolymeric M-blocks (M-M-M), homopolymeric G-blocks (G-G-G) and heteropolymeric, sequentially alternating MG-blocks (G-M-G-M). Alginate forms gels with most di- and multivalent cations. Monovalent cations and Mg2+ ions do not induce gelation while ions like Ba2+ and Sr2+ will produce stronger alginate gels than Ca2+. The gel strength will depend upon the guluronic content and also on the average number of G-units in the G-blocks. Thus, depending on whether a more rigid or flexible structure is desired, the composition of alginic acid or alginates can be adjusted. Modifications of polysaccharides, obtained by derivatisation of the OH functionalities have been described in the art. Thus the term alginate includes alginate derivatives such as, but not limited to dialdehydic alginate, carboxamide alginic acid derivatives (such as 6-O-[(N-2-Deoxy-D-glucose)]carboxamide alginate), methylamine alginic acid derivatives (such as 6-methylamine alginic acid; 2,3-Di-(Methylamine)alginic acid derivatives), diamine alginic acid derivatives (such as 2,3-Di-(Amine)alginic acid, dodecanediamine alginic acid derivatives, 6-Hexanediamine alginic acid derivatives, 2,3-Di-(Hexanediamine)alginic acid derivatives), e-N-Maleimidopropionate alginate; N-Morpholino alginamide, Poly(ethylene glycol)alginate, Succinimidyl alginate, Alginate thioethylamine and Alginate thiocarbohydrazide.

Polysulphated alginate can be obtained from alginic acid using chlorosulphonic acid as a sulphating agent for alginic acid following the procedure described by T. Astrup et al. (Acta Phys. Scand., 1944, 8: 215-226), as described herein. However, it is understood that the use of polysulphated alginate obtained by any method of production is envisaged within the context of the present invention.

The present invention relates to the use of polysulphated alginate in a matrix for human or animal cells. Thus according to a first aspect of the invention, polysulphated alginate is used as a matrix component.

The matrix for use according to the present invention is suitable for human and/or animal cells. This means that the matrix should have the physico-chemical characteristics so as to allow animal and/or human cells to survive and where applicable to multiply in the matrix. As used herein 'cultivation' will refer to either maintaining the cells in a viable state (e.g. as in a carrier function) and/or active stimulation of multiplication (e.g. by repeated passaging) of the cells.

Thus, the matrix according to the present invention is particularly a pharmacologically and biologically acceptable, non-toxic, and biocompatible matrix. Optionally it is moreover a biodegradable or bioresorbable biomatrix. The matrix of the invention can be of an undefined shape and of non-solid material such as a gel, or can be a sheet or a tapered shape.

The matrix can thus comprise any suitable material, including synthetic polymeric material and ground substances. Examples of matrices are the biodegradable and chemically defined calcium sulfate, tricalciumphosphate, hydroxyapatite, Glassfiber.®, plaster of Paris, beta-whitlockite, biodegradable polymers including homopolymers (e.g., poly-paradioxanone, polylysine or polyglycolic acid) and copolymers (e.g., polylactic acid and polyglycolic acid) and combinations thereof. Other potential materials are biodegradable and biologically well defined, such as bone or dermal collagen, alginate, pectin, agarose, and fibrinogen. Other potential matrices are nonbiodegradable and chemically defined, such as sintered hydroxyapatite, bioglass, aluminates, or other ceramics. Matrices may be comprised of combinations of any of the above mentioned types of material. An overview of Biomaterials and their respective properties can be found in Biomaterials, Alpha Science International Ltd., Pangbourne England.

The matrix can be either cross-linked or not, depending on the application. Examples of matrices are described in U.S. Pat. No. 6,514,514, incorporated herein by reference. According to a particular embodiment of the present invention the matrix allows administration of one or more drugs in a gradient to an osteochondral defect, The gradient can correspond to the variable degree of repair needed in the defect and/or to the transition of cartilage (low concentration) to bone (high concentration).

It is an advantage of the matrix of the present invention, that polysulphated alginate shows a much stronger stimulation on the metabolism of connective tissue cells, when compared with polysulphated chondroitin sulphate or polysulphated Xylosan or naturally occurring chondroitin sulphate. Different concentrations of the polysulphated alginate in the matrix are envisaged and can be dependent on the specific application. According to a particular embodiment the polysulphated alginate is present in the matrix in the range of between 100 ng and 500 µg/ml, more particularly in the range between 1 µg and 100 µg/ml of the matrix.

It is an another advantage of the matrix of the present invention, that alginates (including polysulphated alginates) have a superior gel-forming capacity when compared to other polysaccharides and polysulphated polysaccharides. According to a particular embodiment of the invention, the matrix comprising polysulphated alginate further comprises one or more components with a comparable structure to polysulphated alginate, allowing a homogenous distribution thereof within the matrix. Thus, particularly, the matrix further comprises a high molecular weight polysaccharide, most particularly unsulphated (e.g. sodium) alginate, which can be homogeneously mixed with polysulphated alginate. Sodium alginate forms a biodegradable gel when crosslinked with divalent cations and its suitability as a substrate for proliferation of cells in tissue engineering, which can be influenced by its composition, has been described (see Wang et al., 2003, Biomaterials 24:3475-3481). The weight ratio of polysulphated alginate vs. alginate can vary between about 1:1 and about 1:100 or more, a particular embodiment being a ratio of polysulphated alginate vs. alginate of 1:20. In a particular embodiment the weight percentage of polysulphated alginate compared to alginate is between 0.005 and 10%, or the ratio between polysulphated alginate and alginate is between 1/200 and 1/150, between 1/150 and 1/100, between 1/100 and 1/50, between 1/50 and 1/25 or between 1/25 and 1/10. In a particular embodiment, the concentration of polysulphated alginates in the matrix of the present invention is lower than 500 microgram/ml.

Optionally, according to the present invention, the matrix is structured in a particular way so as to direct growth of the cells in a particular pattern. More particularly, the high molecular weight polysaccharide gel comprising the polysulphated alginate of the invention can be designed to contain channels, so that the cells are guided to grow in columns within the matrix (such as described by Aydelotte et al., 1998, In vitro Cell Devel Biol—Animal 34:123-130). This can be of interest in situations where growth of the cells in an organized pattern is beneficial.

Optionally, the matrix of the invention further comprises other polysulphated polysaccharides such as polysulphated cyclodextrin and/or polysulphated inulin, or other components capable of stimulating production of extracellular matrix of connective tissue cells.

Optionally the matrix of the invention further comprises nutrient media, such as, but not limited to MEM, Dulbecco's modified MEM, HAM's F12, Hanks balanced salt solution or mixtures thereof.

Optionally the matrix of the invention can further comprise growth factors which induce or stimulate growth of particular cells. The type of growth factors will be dependent on the cell-type for which the matrix is intended. For instance, in the case of osteochondral cells, the matrix can optionally comprise one or more growth factors such as platelet derived growth factors (PDGF), transforming growth factors (TGF-beta), insulin-like growth factors (IGF), fibroblast growth factors (FGF), epidermal growth factor (EGF), human endothelial cell growth factor (ECGF), granulocyte macrophage colony stimulating factor (GM-CSF), vascular endothelial growth factor (VEGF), cartilage derived morphogenetic protein (CDMP), bone morphogenetic proteins (BMP) such as OP-1, OP-2, BMP2, BMP3, BMP4, BMP9, BMP11-14, DPP, Vg-1, 60A, and Vgr-1.

Optionally, the matrix of the invention can further comprise additional factors which influence the growth and/or activity of particular cells. For instance, in the case of chondrocytes, a factor such as a chondroitinase which stimulates cartilage production by chondrocytes can be added to the matrix in order to maintain chondrocytes in a hypertrophic state (as described in US 20020122790).

According to the present invention, presence of polysulphated alginates in a matrix will enhance the activity and/or growth of the cell type in the immediate vicinity of or embedded in the matrix. The matrix comprising polysulphated alginate according to the present invention is useful as a carrier or for the preservation and/or cultivation of cells in vitro or in vivo.

A particular embodiment of the invention relates to the use of polysulphated alginate in a matrix as a carrier and/or for the cultivation of connective tissue cells or progenitor cells thereof. 'Connective tissue' as used herein refers to any of a number of structural tissues in the body of a mammal including but not limited to bone, cartilage, ligament, tendon, meniscus, dermis, hyperdermis, muscle, fatty tissue, joint capsule.

More specifically, it has been discovered that polysulfated alginate increases aggrecan synthesis and especially the synthesis of aggrecan aggregates by osteochondral cells such as human articular cartilage cells. 'Osteochondral cells' as used herein refers to cells which belong to either the chondrogenic or osteogenic lineage or which can undergo differentiation into either the chondrogenic or osteogenic lineage, depending on the environmental signals. This potential can be tested in vitro or in vivo (De Bari et al. 2001, Arthritis Rheum. 44(1): 85-95; Pittenger et al., 1999, Science 284(5411):143-147; Dell'Acio et al., 2003, Exp. Cell Res. 287(1):16-27). Thus a particular aspect of the invention relates to the use of polysulphated alginate in a matrix for osteochondral cells, more particularly chondrogenic cells, i.e. cells which are capable of producing cartilage or cells which themselves differentiate into cells producing cartilage, including chondrocytes and cells which themselves differentiate into chondrocytes (i.e. chondrocyte precursor cells).

According to one aspect of the invention, a matrix comprising polysulphated alginates is used in the generation (and optionally implantation) of prosthetic devices, such as, but not limited to prosthetic cartilage devices. For instance, chondrocytes can be cultured on biodegradable, biocompatible highly porous scaffolds formed from polymers such as polyglycolic acid, polylactic acid, agarose gel, or other polymers which degrade over time, comprising the polysulphated alginates of the invention. Particularly suitable according to the present invention is a sodium alginate gel comprising polysulphated alginate. The matrices are designed to allow adequate nutrient and gas exchange to the cells until engraftment occurs. The cells can optionally be cultured in vitro (or ex vivo) until adequate cell volume and density has developed for the cells to be implanted. Alternatively, the matrix with cells can be implanted into the body directly. The matrices can be cast or moulded into a desired shape on an individual basis, so that the final product closely resembles the patient's own ear or nose (by way of example), or flexible matrices can be used which allow for manipulation at the time of implantation, as in a joint.

The present invention is of particular use for treating osteochondral defects of a diarthroidal joint, such as knee, an ankle, an elbow, a hip, a wrist, a knuckle of either a finger or toe, or a temperomandibular joint. Such osteochondral defects can be the result of traumatic injury (e.g., a sports injury or excessive wear) or a disease such as osteoarthritis. A particular embodiment relates to the use of the matrix of the present invention in the treatment or prevention of superficial lesions of osteoarthritic cartilage. Additionally the present invention is of use in the treatment or prevention of osteochondral defects which result from aging or from giving birth. Osteochondral defects in the context of the present invention should also be understood to comprise those conditions where repair of cartilage and/or bone is required in the context of surgery such as, but not limited to, cosmetic surgery (e.g. nose, ear). Thus such defects can occur anywhere in the body where cartilage or bone formation is disrupted or where cartilage or bone are damaged or non-existent due to a genetic defect.

Thus, one aspect of the invention relates to a pharmaceutical composition containing a matrix comprising polysulphated alginate. This pharmaceutical composition is of particular use in the treatment or prevention of connective tissue defects, more particularly osteochondral defects. Application of the matrix to the osteochondral defect has a stimulatory effect on the proliferation and production of extracellular matrix by the osteochondral cells present in said defect. Optionally, the matrix can further comprise agents which attract osteochondral cells.

According to the present invention the pharmaceutical composition comprising a matrix comprising polysulphated alginate optionally comprises cells, more particularly connective tissue cells or progenitor cells thereof. Cells for use in the pharmaceutical composition of the invention can be autologous (self) or allogeneic, which can be isolated either from a family member (related) or from one or more unrelated donors. Such cells can be freshly isolated, cultivated or passaged. Optionally such cells can be selected and/or purified based on the expression of particular proteins of interest (such as described in WO 01/24833, WO 01125402, or WO 96/41620 for connective tissue cells). Such cells can be obtained from different origins including but not limited to pre-existing cartilage and subchondral bone, perichondrial tissue, the synovial membrane and bone marrow.

As indicated above, cells suitable for use in the pharmaceutical composition of the invention include precursor cells or progenitor cells of connective tissue cells. Such cells include cells obtained directly or indirectly from bone marrow stromal cells or mesenchymal stem cells but have also been obtained from other tissues such a muscle, heart and granulation tissue.

The cells described above can be present in the pharmaceutical composition of the invention at different concentrations. For instance, cells can be mixed in the gel-like matrix comprising polysulphated alginate at a concentration of between $1\text{-}50\times10^6$ cells per ml.

BRIEF DESCRIPTION OF THE FIGURE

The following Examples, not intended to limit the invention to specific embodiments described, may be understood in conjunction with the accompanying Figure, incorporated herein by reference, in which.

EXAMPLES

Example 1

Preparation of Polysulfated Alginate

Figure 1:
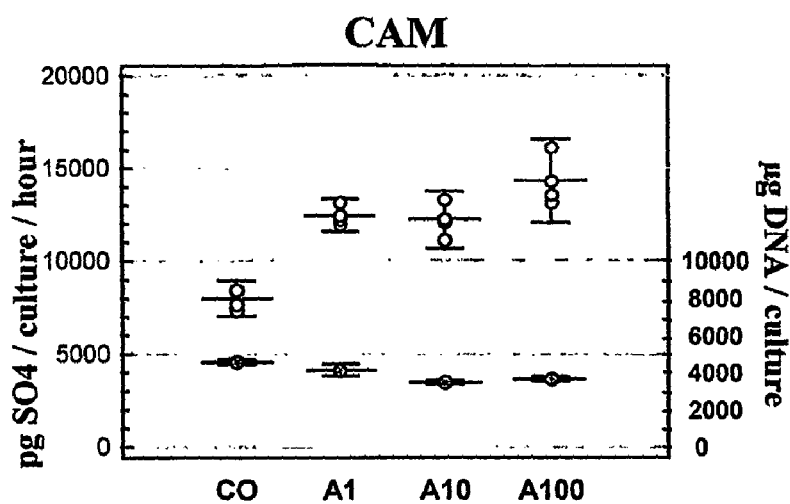
FIG. 1: Newly synthesized $^{35}$sulfated aggrecans by the chondrocytes in culture upon incubation with different concentrations of polysulphated alginate. (A) amount of $^{35}$sulfated aggrecan and DNA measured independently; (B) amount of $^{35}$sulfated aggrecan plotted in relation to amount of DNA measured.
Figure 1:
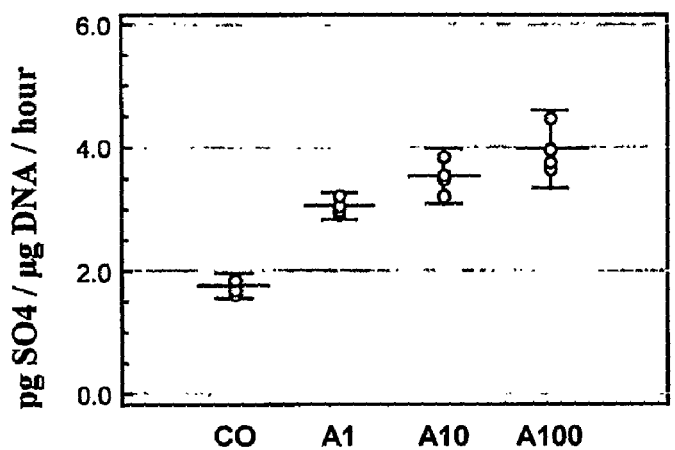

Drop by drop, one vol. of Chlorosulphonic acid is added to 6.6 vol. ice-cold Pyridine. Approx. 300 mg of the alginate is added to 5 ml of the Chlorosulphonic/Pyridine mixture. The solution is then kept at 100° C. during 5 hours. After cooling, 25 ml of distilled water are added. 100 ml of 10% Na-Acetate in methanol are then added to this solution to precipitate the polysaccharide polysulphuric acids. The precipitate is washed 2 times in methanol and dissolved in an appropriate amount of pyrogen free distilled water to remove the remaining Chlorosulphonic acid, Pyridine and buffer salts. The precipitate containing the polysulphated alginate is lyophilized. The polysulphated alginate is recovered as a dry white powder.

The degree of sulphation and purity of the alginate as well as its pyrogen content was determined conventional chemical and biological methods. Under the conditions used, sulphation of alginate was found to be complete.

Example 2

Evaluation of the In Vitro Effects of Polysulphated Alginate on the Synthesis by Human Articular Cartilage Cells of Extracellular Matrix Aggrecans Methodology
Isolation of Chondrocytes
Human articular chondrocytes were isolated as described by W. T. Green Jr (Clin. Orthop., 1971, 75:248-260) and K. E. Kuettner et al. (J. Cell. Biol., 1982, 93:743-750) with a few modifications (M. Cornelissen et al. J. Tiss. Cult. Meth., 1993, 15:139-146).
Incubation with Polysulphated Alginates
The articular cartilage cells were cultured in gelled alginate as described by P. D. Benya et al. (Cell, 1982, 30:215-224). The alginate contained different concentrations of alginate polysulphate prepared as described in Example 1.
Analysis of Aggrecan Synthesis
Synthesis of aggrecans was investigated using $Na_2^{35}SO_4$ as a radioactive precursor for $^{35}$Sulfated newly synthesized aggrecans by the chondrocytes in culture.
After a two-week culture period, 10 µCi/ml of the label was included in the incubation medium over 48 hours. Newly synthesized $^{35}$S-aggrecans partly accumulated in the artificial intercellular agarose matrix. Another part of these $^{35}$S-macromolecules escaped to the incubation medium. The alginate was then solubilized in the culture dish using 3.0 ml of a 55 mM trisodium citrate solution in the presence of proteinase inhibitors at 40° C. overnight. The resulting suspension was centrifuged. The supernatant which contained the interterritorial matrix $^{35}$S-aggrecans, and the incubation medium containing $^{35}$S-aggrecan metabolites that escaped from the extracellular matrix were pooled separately for further chromatography.

The pellet which contained the cells and the cell-associated $^{35}$S-aggrecans, was treated with 1 ml of 4.0 M Guanidinium Chloride in 0.05 M Na-acetate pH 5.8 containing proteinase inhibitors for 48 hours to extract the cell-associated $^{35}$S-aggrecans. The resulting solution was then centrifuged to discard the cells and the supernatant was stored for further chromatography.

After centrifugation, aliquots of nutrient media, alginate digests and pericellular matrix extracts were desalted through Sephadex G25 chromatography gels in 0.067 M phosphate pH 6.8, containing 0.01M $Na_2SO_4$, in order to separate $^{35}$S-labeled aggrecans from free $^{35}$Sulphate. The eluted macromolecular fractions were counted for radioactivity. The radioactivity under the curves (void volume) is related to the total incorporation of $^{35}$Sulphate in aggrecans by the respective cultures. Considering the amount of pooled culture medium that ultimately was analyzed after chromatography, the specific activity of the incubation medium, the decay of $^{35}$Sulphate, the labeling period in hours and the numbers of cells per culture, sulphate incorporation was expressed as pg of $SO_4$ incorporated per $1.10^6$ chondrocytes per hour (G. Verbruggen et al., Osteoarthritis Cart, 2000, 8:170-179).
Analysis of $^{35}$S-Aggrecan Subpopulations
Pools of combined media and agarose digests were desalted through chromatography gels in order to separate $^{35}$S-labeled aggrecans from free $^{35}$Sulphate. Fractions eluted through Sephadex G25 gel and containing the $^{35}$S-labeled macromolecules were pooled and used for gel permeation chromatography on Sepharose CI-2B in the same buffer. $^{35}$S- labeled macromolecules have been shown to elute in three fractions: $^{35}$S-aggrecan aggregates and monomers separated from each other in the first two peaks. Some low molecular weight material (breakdown products; low hydrodynamic size aggrecan subpopulations) eluted in the third tailing fraction. The radioactivity under the first two curves allowed the proportions of $^{35}$S-aggrecan aggregates and monomers to be calculated.

Determination of DNA Content

Proliferation in alginate was followed by measurement of the DNA content in the cultures. DNA content was assayed using the enhancement of fluorescence of trisbenzimidazole (Hoechst 33258) when the latter binds to double stranded DNA (Lebarca C, Paigen K., 1980, Anal. Biochem. 102:344-52). The alginate cultures were therefore liquefied by sonication for 1 minute (MSE ultrasonicator, type 5.65; power set at 100 Watt). To 2 ml of the Hoechst dye solution (0.1 µg/ml in 10 mM Tris. HCl, pH 7.4, 1 mM EDTA and 0.2 M NaCl) 50 µl of the liquefied alginate was added and fluorescence was measured in a Hoefer dynaquant 200 fluorometer, using double stranded calf thymus DNA in liquefied alginate as a standard.

Results

As can be seen in Table 1 the presence of alginate polysulphate at 1-10 µg/ml concentrations in the cultivation media of the chondrocytes provoked a remarkable increase in the synthesis and accumulation of aggrecans in the cell-associated pericellular matrix and in the interterritorial matrix of the chondrocytes.

FIG. 1 furthermore demonstrates that the increased aggrecan synthesis is due to an increased expression of aggrecan by the chondrogenic cells, as the total amount of DNA measured is not increased with the higher concentration of polysulphated alginate used.

TABLE 1

Quantity of $^{35}$S aggrecans (pg SO$_4$ in aggrecan/1*10$^6$ cells/hour)

| Alg-SO$_4$ (µg/ml) | cell-associated matrix | Interterritorial matrix | Culture medium |
|---|---|---|---|
| 0 | 1.315 | 8.036 | 1.589 |
| 1 | 2.262 | 6.232 | 1.658 |
| 10 | 2.907 | 8.232 | 3.873 |
| 100 | 1.373 | 6.589 | 2.187 |

Alg-SO$_4$ = polysulphated alginate

Example 3

Preparation of a Pharmaceutical Composition Comprising Polysulphated Alginates

Example of a formulation of 100 ml of gel containing polysulphated alginate for use as a matrix in the transplantation of human chondrocytes

| | |
|---|---|
| polysulphated alginate (sodium salt) | 100 µg |
| alginate | 1 g |
| double concentrated DMEM antibiotics | 100 ml |

Example 4

Implantation of Sulphated Alginate Seeded with Autologous Chondrocytes under a Periosteal Flap in Cartilage Defects in a Goat Model The present example investigates the repair of standardized cartilage defects by implantation of autologous chondrocytes embedded in a matrix comprising polysulphated alginate.

Adult female non-lactating and not pregnant Saanen goats were used for autologous chondrocyte transplantation. All goats were 3 years or older and derived from CAE (Caprine Arthritis and Encephalitis Virus)-negative certified farms.

Goats cartilage chips were digested enzymatically (hyaluronidase (0.25% in DM) for 1 h, pronase (0.25% in DM) for 1 h, overnight in DM ((DM)=DMEM LG+antibiotics+L-Glutamine)+10% autologous serum, collagenase (0.2% in DM+10% autologous serum) for 34 h) to obtain a single cell suspension. After washing the viability of the isolated cells was assayed by trypan blue exclusion test. All cell populations had a viability above 95%.

TABLE 2 features of isolated autologous goat chondrocytes

| Treatment Group | Animal code | days in culture | cell# mln | harvested cartilage (mg) | cell#/mg cartilage |
|---|---|---|---|---|---|
| ACT in polysulphated alginate | G142 | 7 | 1.7 | Not measured | N/A |
| | G138 | 7 | 3.1 | Not measured | N/A |
| | G132 | 7 | 0.75 | 45 | 16667 |
| | G114 | 7 | 1.2 | 70.2 | 17094 |
| ACT in suspension | G136 | 8 | 5 | Not measured | N/A |
| | G126 | 8 | 0.44 | 20.6 | 21359 |
| | G120 | 8 | 0.75 | 32 | 23438 |
| | G113 | 8 | 3.7 | Not measured | N/A |

Cells were dissolved to a final concentration of 5×10$^6$ cells/ml polysulphated alginate solution. This cell suspension was dropped through a G25 gauge needle into a 102 mM CaCl2 solution for polymerization (10 min). After washing with 0.9% NaCl, polysulphated alginate comprising beads were cultured in DMEM+AB+L−Glut+10% autologous serum until implantation. Final cell concentration per bead: approximately 30000 cells/bead The day of implantation, culture medium was discarded and beads were dissolved in 2ml of a 55 mM Nacitrate solution. After approx. 2 minutes, 10 ml of PBS was added and this solution was centrifuged at 1600 RPM, 10 min to wash. The supernatans was discarded and the cell pellet was resuspended in DMEM+AB+L−Glut+10% autologous serum to a final cell concentration of 5 min/ml. Cell viability was checked by trypan blue exclusion test and was >95%.

A standard volume of cartilage defect (6 mm diameter) was filled. The defect was sealed with a 8-10 mm diameter periosteal flap and sealed with fibrin glue (Quixil®—Omrix Biopharma).

Left and right femoral condyles were assayed after about 13 weeks. The Synovium was stained with hematoxylin and eosin staining, The condyles were stained with hematoxylin and eosin staining staining, Toluidine Blue staining and Safranin O.

The microscopic evaluation of the cartilage repair is summarized in table 3:

TABLE 3 cartilage formation after ACT procedure in goats

| Treatment Group | Animal code | results |
|---|---|---|
| ACT in polysulphated alginate | G142 | poor repair |
| | G138 | procedure failed |
| | G132 | partial filling of defect with hyaline-like cartilage showing some good organisation |
| | G114 | newly formed cartilage in repair zone |
| ACT in suspension | G136 | procedure failed |
| | G126 | procedure failed |
| | G120 | early signs of osteoarthritis, but some repair tissue with a certain structure. Interpretation of outcome is difficult |
| | G113 | poor repair |

The invention claimed is:

1. An in vitro/ex vivo method for the cultivation of chondrogenic cells, comprising the step of contacting said cells with a matrix comprising 1 to 10 μg/ml polysulphated alginate and culturing the chondrogenic cells, wherein said matrix is for implantation into a human or animal body and repair of a cartilage defect.

2. The method according to claim 1, wherein said matrix further comprises nutrient media.

3. The method according to claim 1, wherein said matrix comprising 1 to 10 μg/ml polysulphated alginate, further comprises unsulphated alginate.

4. The method according to claim 3, wherein said polysulphated alginate and said unsulphated alginate are present in a weight ratio of between 1:1000 and 1:10,000.

5. The method according to claim 1, wherein said chondrogenic cells are chondrocyte precursor cells.

6. A matrix comprising 1 to 10 μg/ml polysulphated alginate and cultured chondrogenic cells wherein said matrix is for implantation into a human or animal body and repair of a cartilage defect.

7. The matrix of claim 6, which further comprises nutrient media.

8. The matrix of claim 6, which further comprises unsulphated alginate.

9. A pharmaceutical composition comprising a matrix, said matrix comprising cultured chondrogenic cells and 1 to 10 μg/ml polysulphated alginate wherein said composition is for implantation into a human or animal body and repair of a cartilage defect.

10. A method for the treatment of a cartilage defect, said method comprising 1 to 10 μg/ml administering to the cartilage defect a matrix comprising polysulphated alginate and cultured chondrogenic cells.

11. The method according to claim 1, wherein said chondrogenic cells are chondrocytes.

12. The matrix according to claim 6, wherein said chondrogenic cells are chondrocytes.

13. The matrix of claim 6, wherein said chondrogenic cells are chondrocyte precursor cells.

14. The pharmaceutical composition according to claim 9, wherein said chondrogenic cells are chondrocytes.

15. The pharmaceutical composition according to claim 9, wherein said chondrogenic cells are chondrocyte precursor cells.

16. The method according to claim 10, wherein said chondrogenic cells are chondrocytes.

17. The method according to claim 10, wherein said chondrogenic cells are chondrocyte precursor cells.

* * * * *

UNITED STATES PATENT AND TRADEMARK OFFICE
CERTIFICATE OF CORRECTION

PATENT NO. : 7,988,962 B2  Page 1 of 1
APPLICATION NO. : 10/595821
DATED : August 2, 2011
INVENTOR(S) : August Verbruggen et al.

It is certified that error appears in the above-identified patent and that said Letters Patent is hereby corrected as shown below:

In claim 10, column 12, line 16, after "comprising" and before "administering," delete
"1 to 10 µg/ml".

In claim 10, column 12, line 17, after "comprising" and before "polysulphated," insert
--1 to 10 µg/ml--.

Signed and Sealed this
Twentieth Day of September, 2011

David J. Kappos
*Director of the United States Patent and Trademark Office*